US00PP10364P

United States Patent [19]

Utecht

[11] Patent Number: Plant 10,364

[45] Date of Patent: Apr. 28, 1998

[54] GERANIUM PLANT NAMED 'FISSAMBA'

[75] Inventor: Angelika Utecht, Montabaur, Germany

[73] Assignee: Florfis AG, Binningen, Switzerland

[21] Appl. No.: 754,363

[22] Filed: Nov. 22, 1996

[51] Int. Cl.[6] ..... A01H 5/00

[52] U.S. Cl. ..... Plt./87.12

[58] Field of Search ..... Plt./87.12

[56] References Cited

PUBLICATIONS

GTITM LIPOVROM –Citation DE PBR PEL 01013 for 'Fissamba', Dec. 18, 1995.

GTITM LIPOVROM –Citation CA PBR 96–796 for 'Fissamba', Jul. 29, 1996.

*Primary Examiner*—James R. Feyrer

*Attorney, Agent, or Firm*—Foley & Lardner

[57] ABSTRACT

A new and distinct cultivar of geranium plant named 'Fissamba', particularly characterized by the combined features of bright red flowers arranged tightly in compact, almost spherically shaped umbels, medium green foliage with distinct zonation, medium growth habit and early flower response.

1 Drawing Sheet

The present invention comprises a new and distinct cultivar of geranium, botanically known as Pelargonium zonale, and hereinafter referred to by the cultivar name 'Fissamba'.

'Fissamba' is a product of a planned breeding program which had the objective of creating new geranium cultivars with red flower color, medium green, zoned foliage, and medium sized plant habit.

'Fissamba' was originated from a hybridization made by the inventor Angelika Utecht in a controlled breeding program in Galdar, Gran Canaria, Spain, in 1991. The female parent was the cultivar 'Fisnida', characterized by single orange-red flowers, and medium green foliage with distinct zonation. The male parent of 'Fissamba' was the commercial variety 'Robe', having dark cherry red semi-double flowers, and light to medium green foliage with weak zonation.

'Fissamba' was discovered and selected as one flowering plant within the progeny of the stated cross by Angelika Utecht in 1992 in a controlled environment in Galdar, Gran Canaria, Spain. The first act of asexual reproduction of 'Fissamba' was accomplished when vegetative cuttings were taken from the initial selection in Autumn 1990 in a controlled environment in Galdar, Gran Canaria, Spain, by, or under the supervision of, Angelika Utecht.

Horticultural examination of plants grown from these cuttings initiated in May 1993 in Hillscheid, Federal Republic of Germany and continuing thereafter, has demonstrated that the combination of characteristics as herein disclosed for 'Fissamba' are firmly fixed and are retained through successive generations of asexual reproduction.

'Fissamba' has not been observed under all possible environmental conditions. The phenotype may vary significantly with variations in environment such as temperature, light intensity and day length, without, however, any variation in genotype.

The following observations, measurements, and comparisons describe plants grown in Hillscheid, Federal Republic of Germany under greenhouse conditions which approximate those generally used in commercial practice.

The following traits have been repeatedly observed and are determined to be basic characteristics of 'Fissamba', which in combination distinguish this geranium as a new and distinct cultivar:

1. Bright red flower color with good stability.
2. Round, weakly semi-double flowers, in compact, almost spherically shaped inflorescences.

3. Medium green foliage with distinct zonation.
4. Medium sized, compact plant habit.
5. Early flower response.

Of the many commercial cultivars known to the present inventor, the most similar in comparison to 'Fissamba' are the parent cultivars 'Fisnida' and 'Robe', and the cultivar 'Fiscrid', disclosed in Plant Pat. No. 8,726.

In general comparison to its parent cultivars, 'Fissamba' has an intermediate flower color, an intense bright red with less orange than 'Fisnida', but lighter and with less bluish tint than 'Robe'. 'Fissamba' has distinctly zoned foliage, similar to 'Fisnida', but stronger than the leaves of 'Robe'. In further comparison to 'Fisnida', 'Fissamba' has semi-double rather than single flowers, a shorter plant habit with smaller inflorescences on weaker peduncles, and an earlier spring flowering response.

In comparison to 'Fiscrid', 'Fissamba' has a slightly darker flower color, smaller diameter umbels, fewer petals per flower, more distinct zonation, smaller leaves, a less spreading plant habit, and an earlier flower response.

The accompanying photographic drawing shows typical flower and foliage characteristics of 'Fissamba', with colors being as true as possible to illustrations of this type.

In the following description color references are made to The Royal Horticultural Society Colour Chart (RHS). The color values were determined indoors from flowers taken from plants grown in a greenhouse in May 1995 in Hillscheid, Germany.

Classification:

*Botanical.*—A hybrid of the species *Pelargonium zonale l'hert.*

*Commercial.*—Zonal geranium, cv. 'Fissamba'

Inflorescence

Umbel:

*Shape.*—Semi-spherical to spherical.

*Average diameter.*—91 mm.

*Average depth.*—51 mm.

*Peduncle length.*—139 mm.

*Pedicel length.*—20 mm.

*Pedicel color.*—Mainly dark red.

*Number of flowers per umbel.*—About 30–40.

Corolla:

*Average diameter.*—47 mm.

*Form.*—Semi-double.

*Number of petals.*—7–11.

*Number of petaloids.*—2.

*Color (general tonality from a distance of three meters)*.—Bright red.

*Color of upper petals.*—44 A.

*Markings on upper petals.*—No markings.

*Color of lower petals.*—45 B.

*Color of lower surface of petals.*—43 A.

*Color of sepals.*—Green, red at base.

*Number of sepals.*—5–6.

Bud:

*Shape.*—Broad elliptic.

*Color (adaxial).*—Light green.

*Color (abaxial).*—Rose-red to red.

Reproductive organs:

*Androecium.*—5–7 fertile anthers, white and pink filaments, orange pollen.

*Gynoecium.*—5–6 lobed stigma, red style and stigma.

*Seed set.*—A few seeds are occasionally developed.

Spring flowering response period: In Hillscheid, Germany in 1995, plants had on average 1.0 flowers opened 11 weeks after planting of unrooted cuttings.

Outdoor flower production: The flower count in 1994 in Hillscheid, Germany indicated about 28 umbels per plant for May through August observation period.

Durability: Good shatter resistance.

Plant

Foliage

*Form.*—Kidney-shaped.

*Margin.*—Bicrenated.

*Upper surface.*—Medium green, approximately 137 A.

*Size of leaf.*—78 mm.

*Color of upper surface.*—Medium green, approximately 137 C.

*Color of zonation.*—Brown, about 166 A.

*Tolerance of botrytis.*—Average.

General appearance and form:

*Internode length.*—10–20 mm.

*Branching pattern.*—4.6 branches per plant, based on 16 week old plants.

*Height of foliage.*—16 cm, measured in June on 16 week old plants.

I claim:

1. A new and distinct cultivar of geranium plant named 'Fissamba', as illustrated and described.

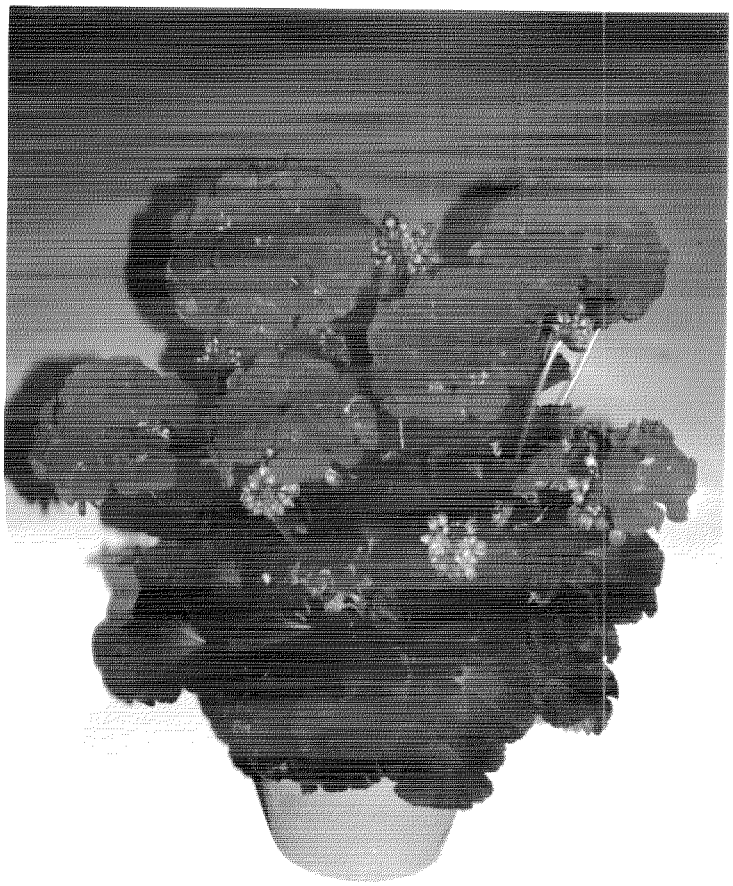

* * * * *